(12) United States Patent  
Hoke et al.

(10) Patent No.: US 7,981,077 B2
(45) Date of Patent: Jul. 19, 2011

(54) SYSTEMS AND METHODS FOR NASAL LAVAGE

(75) Inventors: Martin R. Hoke, Lakewood, OH (US); Robert D. Schilling, Olmsted Township, OH (US); Gary R. Austin, Euclid, OH (US); Jess Paul Carlson, Chagrin Falls, OH (US)

(73) Assignee: RhinoSystems, Inc., Lakewood, OH (US)

( * ) Notice: Subject to any disclaimer, the term of this patent is extended or adjusted under 35 U.S.C. 154(b) by 0 days.

(21) Appl. No.: 12/635,253

(22) Filed: Dec. 10, 2009

(65) Prior Publication Data

US 2010/0152653 A1 Jun. 17, 2010

Related U.S. Application Data

(60) Provisional application No. 61/121,643, filed on Dec. 11, 2008.

(51) Int. Cl.
*A61M 37/00* (2006.01)

(52) U.S. Cl. .................................................. 604/94.01

(58) Field of Classification Search ............... 604/94.01, 604/30, 31, 48, 80, 128
See application file for complete search history.

(56) References Cited

U.S. PATENT DOCUMENTS 1,607,726 A * 11/1926 De Suszko ...................... 604/32
D270,283 S * 8/1983 Goodnow et al. ............ D24/110

* cited by examiner

*Primary Examiner* — Nicholas D Lucchesi
*Assistant Examiner* — Brooke Matney
(74) *Attorney, Agent, or Firm* — Fay Sharpe LLP (57) ABSTRACT

A nasal lavage device includes a source of saline solution, an effluent receptacle, and a nasal interface for engaging the nostrils of a user of the device. A fluid passageway is disposed to communicate the source of saline solution with the effluent receptacle through the nasal cavity of the user. The nasal interface and fluid passageways are included within a removable cartridge for communicating the saline relative to the nostrils in a first direction. A second cartridge can be inserted to communicate the flow in a second direction. The interface includes nasal pillows that form a seal against the user's nostrils.

14 Claims, 8 Drawing Sheets

SYSTEMS AND METHODS FOR NASAL LAVAGE

This application claims the priority benefit of U.S. application Ser. No. 61/121,643, filed Dec. 11, 2008, the disclosure of which is incorporated herein by reference in its entirety.

TECHNICAL FIELD

The presently disclosed embodiments generally relate to methods and devices for lavaging, irrigating, rinsing, and hydrating the nasal cavity and anatomical openings thereto, generally and popularly known as nasal lavage or nasal irrigation.

BACKGROUND

Nasal and sinus disease and sinus related syndromes and symptoms are a common clinical problem with considerable patient morbidity, substantial direct costs, and a significant, negative impact on the quality of life for those who are afflicted. The four primary categories of afflicted groups are: 1) individuals with acute and chronic rhinosinusitis; 2) individuals with upper respiratory infections, 3) individuals who suffer from allergic rhinitis; and 4) individuals with chronic snoring problems. These four categories amount to millions of people who suffer from nasal congestion on a daily basis.

The Centers for Disease Control and Prevention estimated the number of cases of chronic rhinosinusitis in the United States to be 35 million in 1994, a prevalence of about 13.5%, or about 40.5 million Americans adjusted for 2007 population figures (estimates from the National Health Interview Survey, 1994. *Vital Health Stat* 10. 1995: 261-520). Rhinosinusitis was the fifth most common diagnosis for which antibiotics were prescribed from 1985 to 1992 (McCaig L F, Hughes J M. Trends in antimicrobial drug prescribing among office-based physicians in the United States. *JAMA*. 1995; 273:214-219). In 1996 rhinitis accounted for approximately 26.7 million office and emergency department visits resulting in $5.8 billion in direct costs (Ray N F, Baraniuk J N, Thamer M, et al. Healthcare expenditures for sinusitis in 1996: contributions of asthma, rhinitis, and other airway disorders. *J Allergy Clin Immunol.* 1999; 103:408-414).

Allergic rhinitis has been reported to affect approximately 17% of the general population in the United States (Ray N F, Baraniuk J N, Thamer M, et al. Healthcare expenditures for sinusitis in 1996: contributions of asthma, rhinitis, and other airway disorders. *J Allergy Clin Immunol.* 1999; 103:408-414), and in selected pediatric populations, allergic rhinitis might be present in up to 42% (Wright A L, Holberg C J, Martinez F D, Halonen M, Morgan W, Taussig L M. Epidemiology of physician-diagnosed allergic rhinitis in childhood. Pediatrics 1994; 94:895-901). This amounts to an upper estimate of 60 million Americans.

According to the National Sleep Foundation, snoring currently affects approximately 90 million American adults, 37 million on a regular basis.

The combined number of those who suffer from rhinosinusitis, allergic rhinitis, and snoring amounts to a high estimate of 190 million Americans and a low estimate of 128 million Americans, not accounting for double-counting individuals who may be in two or more categories. Adopting the conservative assumption of over 40% duplication yields an estimate of 75 million Americans who suffer from adverse sinus symptoms and would benefit from an effective therapy to relieve those symptoms.

Bathing the nasal and sinus cavities with lightly-salted water to wash away encrusted mucous, irritants, and foreign particles, and to shrink the turbinates for the purpose of improving airflow and relieving nasal congestion has been widely practiced across many cultures for literally thousands of years. More recently, and particularly since about 1990, a significant number of peer-reviewed clinical trials have been undertaken at leading American and European medical schools and research centers testing whether the anecdotal claims of relief from the symptoms of nasal maladies as a result of practicing nasal irrigation, are well founded and pass scientific scrutiny. (Harvey R, Hannan S A, Badia L, Scadding G. Nasal saline irrigations for the symptoms of chronic rhinosinusitis. *Cochrane Database of Systematic Reviews* 2007, Issue 3. Art No.: CD006394. DOI: 10.1002/14651858.CD006394.pub2.)

Several clinical studies demonstrate that regular use of nasal irrigation is an effective therapy to relieve the symptoms of chronic and acute rhinosinusitis, including statistically significant findings of reduced nasal congestion, increased nasal passage airflow, reduced doctor visits, reduced number of prescriptions for sinus medicine, and improved quality of life. (Rabago D, Zgierska A, Mundt M, et al. Efficacy of daily hypertonic saline nasal irrigation among patients with sinusitis: A randomized controlled trial. *Journal of Family Practice.* 2002; 51(12):1049-1055.) Other clinical studies indicate that regular nasal irrigation is a beneficial therapy for the treatment of allergy-related nasal symptoms. (Garavello W, Romagnoli M, Sordo L, et al. Hypersaline nasal irrigation in children with symptomatic seasonal allergic rhinitis: a randomized study. *Pediatric allergy and immunology.* 2003; 14:140-143.) Other as yet unpublished clinical studies are currently underway testing whether nasal lavage is an effective preventive therapy with respect to the common cold and snoring.

These studies indicate that nasal irrigation is a clinically proven method for treating the symptoms of sinus-related disease by exposing the nasal cavity to a streaming volume of saline. While the exact mechanism by which nasal irrigation's effectiveness is achieved is not yet well understood by the medical and scientific research community, it is likely multifaceted and includes a number of physiological effects which individually or in concert may result in an improved ability of the nasal mucosa to reduce the pathologic effects of inflammatory mediators and other triggers of allergic rhinitis, asthma and other chronic mucosal reactions, as follows. First, it rinses the entire interior of the nasal cavity, washing away encrustations that may be blocking the multiple ostia that connect the sinus cavities to the nasal cavity, thereby allowing the sinus cavities to properly drain into the nasal cavity and making the sinus cavities a much less attractive breeding ground for the colonization of bacteria. Second, it decreases the viscosity of the mucous in the nasal cavity, thereby greatly reducing the formation of interior encrustations. Third, it leaves a small residue of saline on the interior surfaces of the nasal cavity, including the openings to the sinus cavities and sometimes in the sinus cavities themselves. This is beneficial because saline has an inherently antiseptic quality that hinders the growth of bacteria. Fourth, exposure of the turbinates, vascular tissue that warms and humidifies the air inspired through the nose before it reaches the lungs, to saline causes them to reduce in size, thereby reducing nasal congestion. Fifth, it improves mucociliary clearance as a result of increased ciliary beat frequency, which improves the ability of the mucosa to perform its natural, flushing function. Sixth, the saline may wash away airborne bacteria, viral particles, irritants and other foreign particles that cause infections and allergies. (See: Ponikau J U, Sherris D A, Kephart D M, et al. Striking deposition of toxic eosinophilic major basic protein in mucus: Implications for chronic rhinosinusitis. *J Allergy Clin Immunol.* 2005; 116(2):362-369.; Ozsoylu S. Nose drops and the common cold. *Eur J Pediatr.* 1985; 144:294.; Karadag A. Nasal saline for acute sinusitis. *Pediatrics.* 2002; 109:165.; Kurtaran H, Karadag A, Catal F, et al. A reappraisal of nasal saline solution use in chronic sinusitis. *Chest.* 2003; 124:2036-2037.; Georgitis J W. Nasal hyperthermia and simple irrigation for perennial rhinitis. Changes in inflammatory mediators. *Chest.* 1994; 106:1487-1492.; Talbot A R, Herr T M, Parsons D S. Mucocilliary clearance and buffered hypertonic saline solution. *Laryngoscope.* 1997; 107:500-503.; Boek W M, Graamans K, Natzijl H, et al. Nasal mucociliary transport: New evidence for a key role of ciliary beat frequency. *Laryngoscope.* 2002; 112:570-573.)

There are two methods by which the nasal cavity can be irrigated: pressure that is positive relative to atmospheric pressure, and pressure that is negative relative to atmospheric pressure. Positive pressure can be effected two ways: first, by gravity, and second, by means of manufactured pressure. Negative pressure, also called vacuum or suction, can also be effected two ways: first, anatomically by nasal inhaling or sniffing, and second, by means of manufactured suction.

Positive pressure devices that rely on gravity allow the flow of saline into the nasal cavity by, for example, inserting the tip of a teapot-like spout into one nostril and pouring the saline into it. The saline then flows around the posterior margin of the nasal septum and out the other nostril of the user. An example of a gravity-based device is the neti pot. However, the awkward physical position required to accomplish such a rinse is difficult for many people, and the free flowing effluent from the nasal passageway is messy so that substantial clean up procedures are necessary.

Positive pressure devices that rely on manufactured pressure pump the saline into the nasal cavity, again, by introducing the saline into one nostril, forcing it under manufactured pressure around the posterior margin of the nasal septum, and allowing it to drain out the other nostril. This can be achieved, for example, by placing the nozzle of a saline-filled, flexible plastic bottle into one nostril and squeezing it, thereby injecting the saline into one nostril, through the nasal cavity, and out the other nostril. This can also be achieved by similarly forcing saline into the nasal cavity under pressure created by a mechanical pump. Although this method avoids some of the physical awkwardness needed to achieve a gravity forced flow, the problems of messiness and the attendant inconvenience of cleaning remain. In addition, the varied pressures imparted by a squeeze bottle can impart undesired, painful, and even harmful pressures throughout the nasal passageway, and particularly on the Eustachian tube ostia. Thus, this requires some acquired skill for proper use.

Earlier nasal lavage devices that relied on negative, manufactured pressure drew a saline solution through the nasal cavity by imparting suction to a receptacle bottle or directly to the nasal cavity, but such devices are large, non-portable, complex, difficult to operate, and generally require the supervision and assistance for operation of an attending physician or medical assistant.

There is presently no practical device that offers a user the ability to practice nasal lavage using either or both positive and negative pressure, whether gravitational, anatomical, or manufactured, or any combination thereof, in a single hand-held device.

There is presently no practical device that offers a user the ability to practice nasal lavage using either or both positive and negative pressure, whether gravitational, anatomical, or manufactured, or any combination thereof, in a single, hand-held, powered device.

There is presently no practical, self-contained device utilizing separate supply and effluent vessels that offers a user the ability to practice nasal lavage using either or both positive and/or negative pressure, whether gravitational, anatomical, or manufactured, or any combination thereof, in a single, handheld, powered device.

There is presently no practical, self-contained device utilizing separate supply and effluent vessels that offers a user the ability to practice nasal lavage using either or both positive and/or negative pressure, whether gravitational, anatomical, or manufactured, or any combination thereof, in a single, handheld, portable, powered device.

There is a need for a convenient hand-held device that can safely irrigate the nasal cavity with a controlled, gentle supply, draw the irrigant through the nasal cavity under the influence of gentle powered suction, collect the effluent safely in a manner facilitating quick and easy disposal, and is readily adaptable to a wide variety of nasal dimensions.

SUMMARY

A nasal lavage device is provided for therapeutic irrigation of a nasal cavity of a user. The device includes a source of saline solution, an effluent receptacle, a nasal interface, a vacuum source, fluid passageways, and a switch and valve assembly. The fluid passageways include a removable cartridge capable of effectuating flow reversal through alternative conduit arrangements. Such a removable cartridge allows a personalizable fit for individual users, is easily washable, and further includes seats for removable nasal pillows or domes, which pillows can be sized to accommodate individual physical requirements due to different nostril dimensions.

DETAILED DESCRIPTION

The Figures show a nasal lavage device or tool, preferably easily hand-held in use, which provides a more convenient, cleaner, more pleasant, and more effective irrigating therapy for the nasal cavity and sinus ostia. The device 10 is principally comprised of three components, an irrigant source bottle 12, containing, for example, saline solution, a receptacle bottle 14 for receiving saline effluent, and a controller 16 for controlling the communication of fluid from the first bottle, through the nasal cavity, and into the second bottle as will be hereinafter more fully explained. The bottles 12, 14 may be of any of a variety of shapes and may be attached to the controller in any variety of manners, such as with a threaded neck, a pinch fit, a bayonet mount, or the like. A typical size will accommodate 6 to 12 ounces of fluid. It is envisioned that in one embodiment the first bottle 12, upon being emptied as the result of having been used, can subsequently be used as the second bottle 14 which upon being filled with effluent by use can then be thrown away. Accordingly, in this embodiment the provision of a single bottle provides both the first bottle of saline source at one time, and then the effluent receptacle 14 at a next time. It is also within the intended scope of the present embodiments that either or both of the bottles may be refillable or reusable, or may even be permanent chambers within the controller 16 that may be filled or emptied upon completion of an irrigating therapy. Although saline solution is mentioned here as the exemplary irrigant, the embodiments are intended to include alternate irrigants of a variety of saline mixes including flavorants, aromatics, probiotics or medicines.

Figure 1:
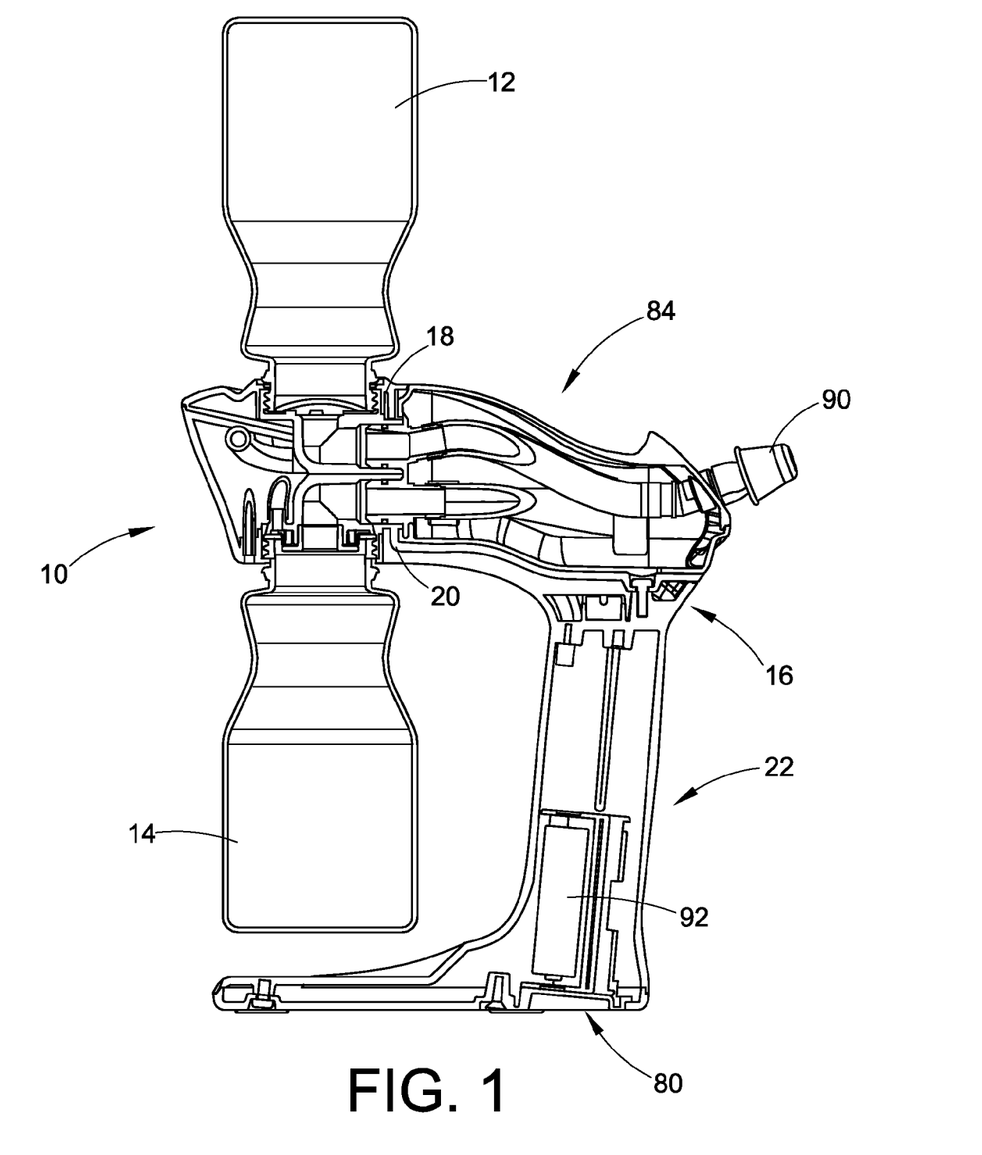
FIG. 1 is an elevated cross-sectional view of one embodiment of the subject nasal irrigation system.
Figure 2:
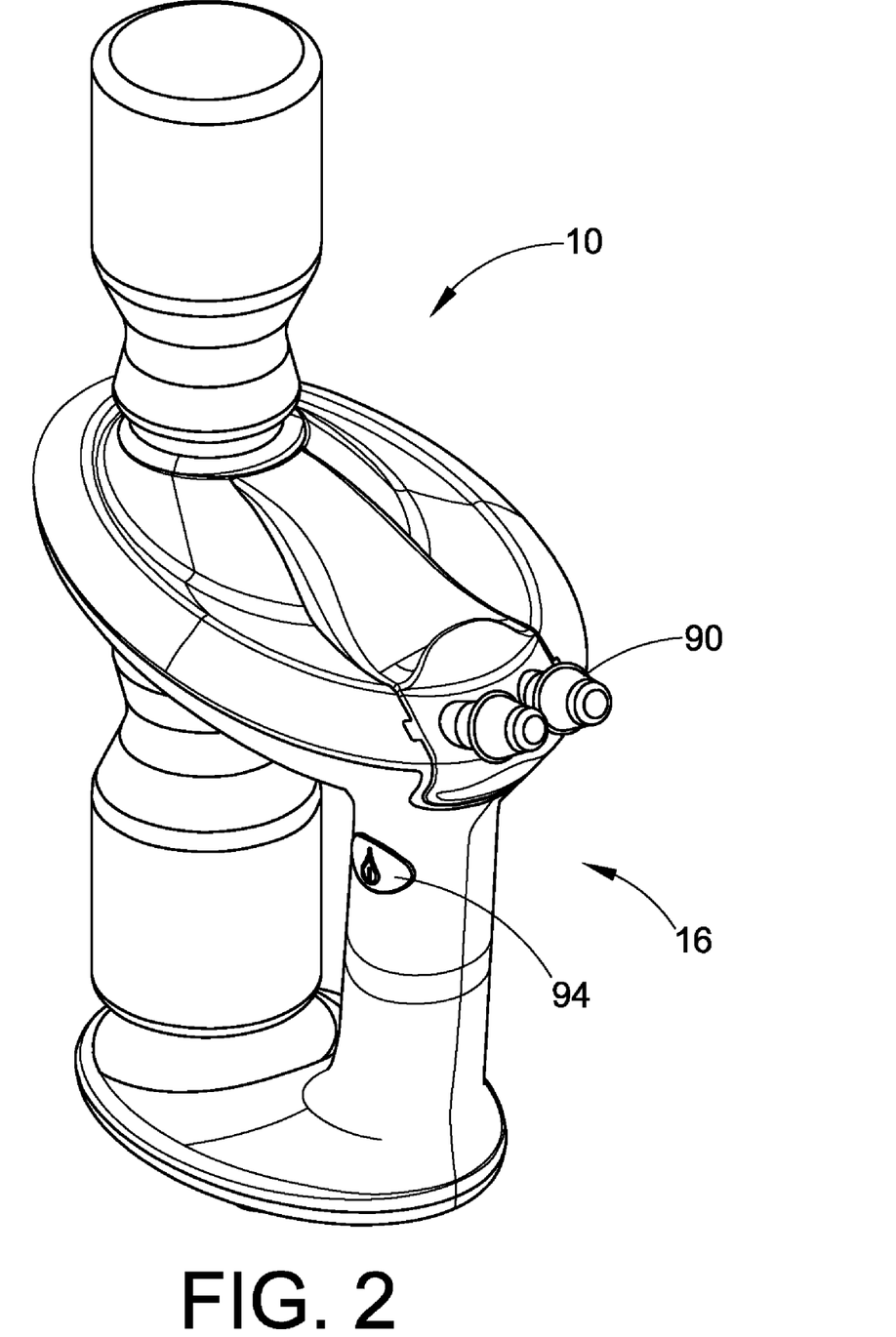
FIG. 2 is a perspective view of the system of FIG. 1.

With particular reference to FIG. 1, it is intended in the present embodiment of this subject nasal lavage system that the source bottle 12 and the receptacle bottle 14 are disposed vertically directly over each other for purposes of facilitating gravitational flow from bottle 12 to bottle 14 and for holding the controller 16 close to a user's nose in a manner that both optimizes the user's physical control of the device, and allows the user to view the depletion of the supply bottle 12 as the system is being used. Supply receiver 18 and effluent receiver 20 threadedly receive the bottles 12, 14 and include conduits or ports, respectively, which comprise the beginning and ending of the fluid passageway.

The structure of the supply receiver 18 such that it allows the supply bottle 12 to be vented to atmosphere. The supply receiver 18 includes a threaded neck with bottom wall protrusions that prevent the neck of the supply bottle from bottoming out on the floor of the receiver 18, thereby providing an air space to allow air to vent and bubble into the bottle 12 as the saline fluid flows out. Also, the threads of the receiver 18 do not match the pitch of the threads of the supply bottle 12, in order to allow air to pass through and circulate along the thread path from the atmosphere into the supply bottle 12. The surface tension of the saline solution through the arcuate threaded path along receiver threads precludes leaking of supply saline from the receiver 18.

The effluent receiver 20 includes a sealing o-ring, a baffle, and a shield. Receiver 20 includes a vacuum port to allow the pump 120 to impart a slight vacuum to the effluent bottle 14, as will be more fully explained below. The baffle and shield form a tortuous path that functions to preclude the saline effluent that is being intentionally drawn into bottle 14 from also being unintentionally drawn into the vacuum port and ultimately into the pump 120. The core of shield through which the effluent saline passes, may be tapered from top to bottom such that its interior diameter is smaller at the bottom, in order to increase the velocity of the effluent saline and thereby decrease the probability that it will adhere to the sides of the shield as it passes through it. The circular tip of the shield preferably comes to a knife edge to reduce surface area and similarly decrease the probability that effluent saline will cling to the tip due to its surface tension.

Figure 3:
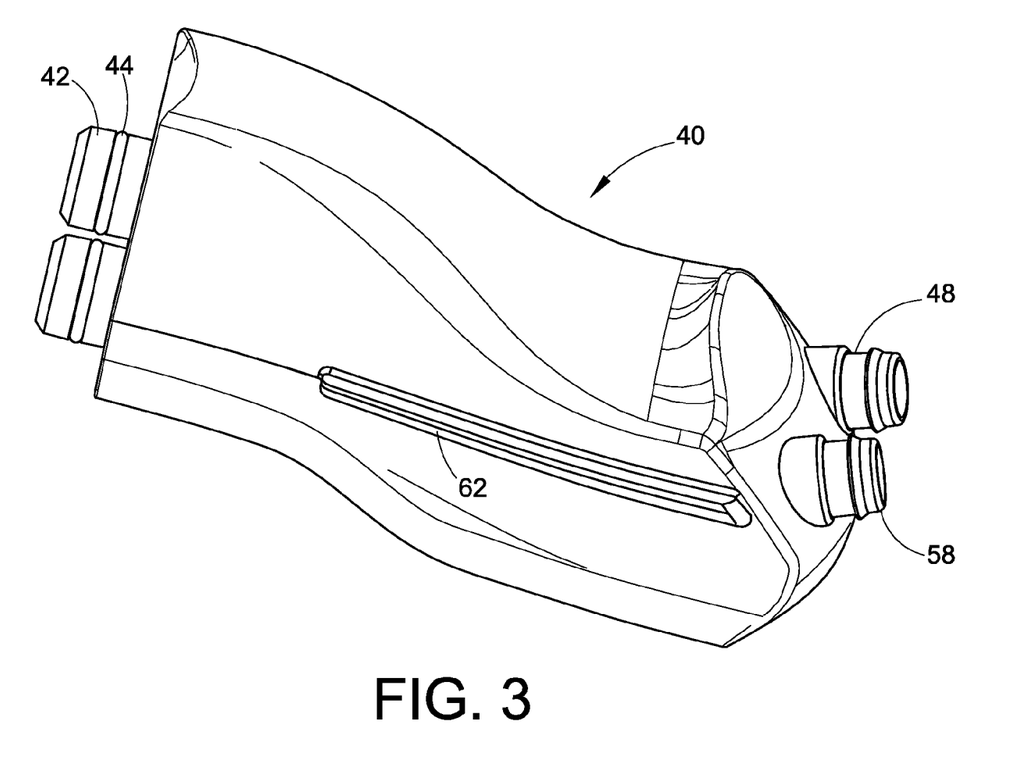
FIG. 3 shows a removable nasal interface cartridge which is intended to engage the receivers of FIGS. 1 and 2 and form a completely enclosed fluid passageway to communicate fluid to and from the nasal cavity of a user.
Figure 4:
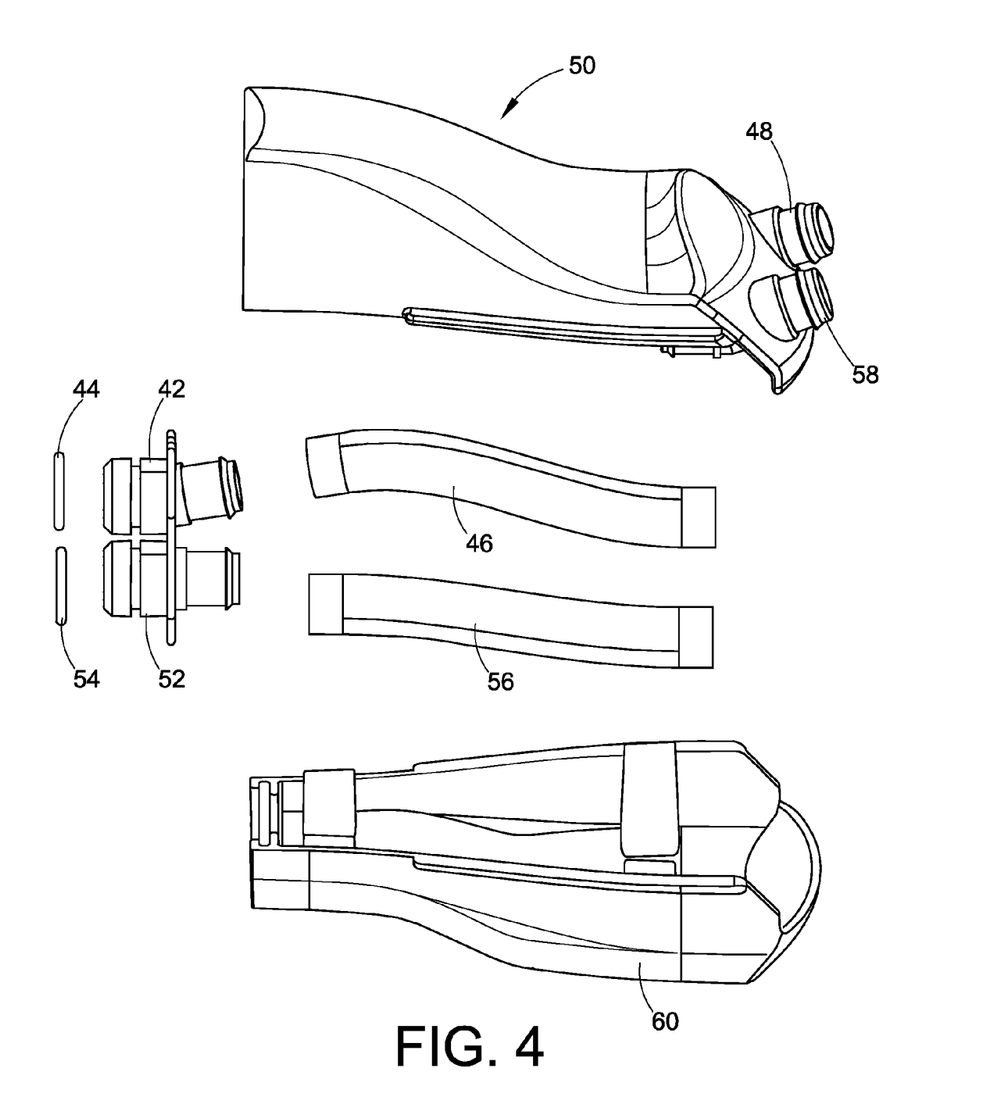
FIG. 4 is an exploded view of the removable cartridge of FIG. 3.

In FIGS. 3 and 4, a removable cartridge 40 for transporting the saline from the supply receiver 18 to the effluent receiver 20, is shown. In particular, a male supply port inlet 42 is inserted in a supply receiver outlet port and sealed by o-ring 44. Member 42 is connected to fluid tube 46 which is connected at its other end to nasal pillow seat 48 extending from cartridge upper housing 50. Effluent receiver inlet port 24 similarly receives a male effluent port outlet 52 which is sealed therein via o-ring 54. Flexible tube 56 connects member 52 with nasal pillow seat 58. Members 42,52 are fixedly received in the cartridge 40 when the upper housing is secured to the lower housing 60. A projection on the sidewall of the cartridge 40 aligns the cartridge into closed receptacle in the handle 16 in a tongue-and-groove manner.

Figure 6:
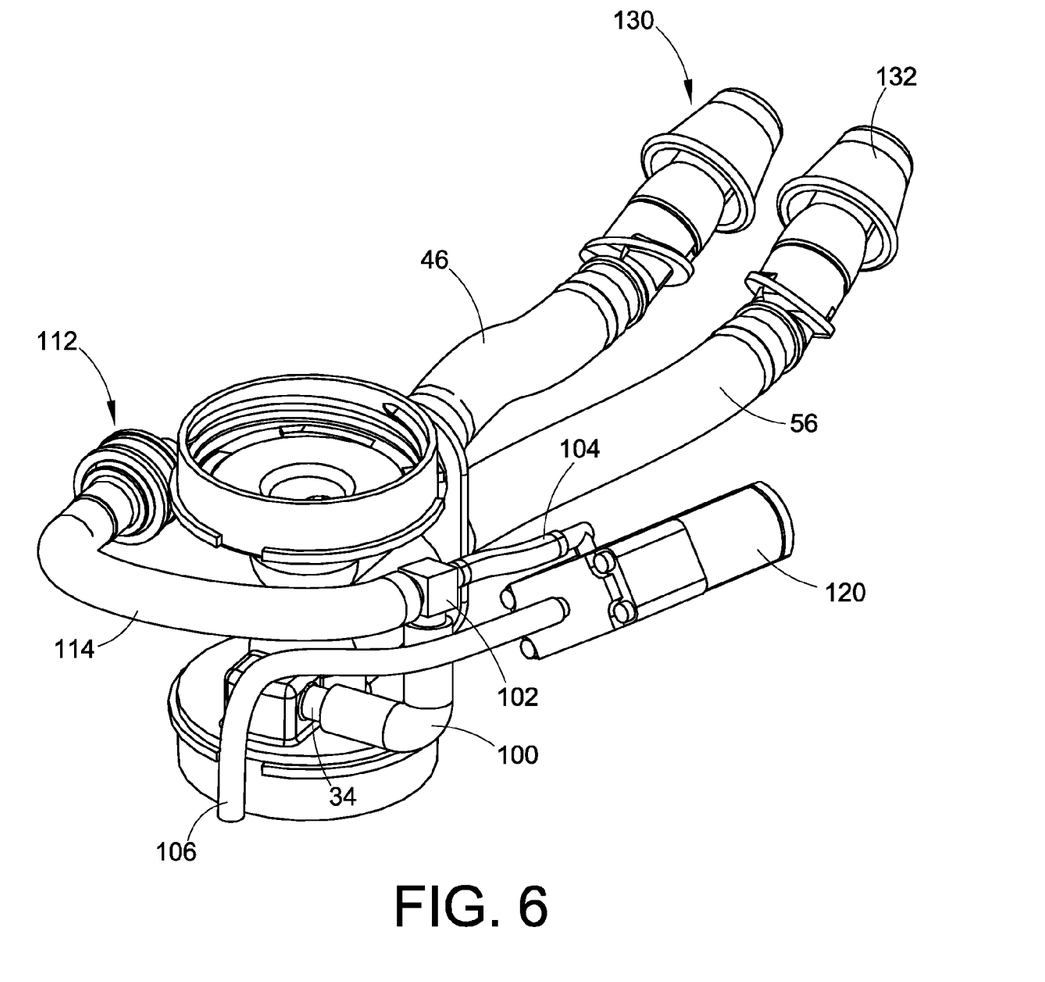
FIG. 6 is an elevated view of the fluid passageways and pressure conduits relative to the caps and pump
Figure 7:
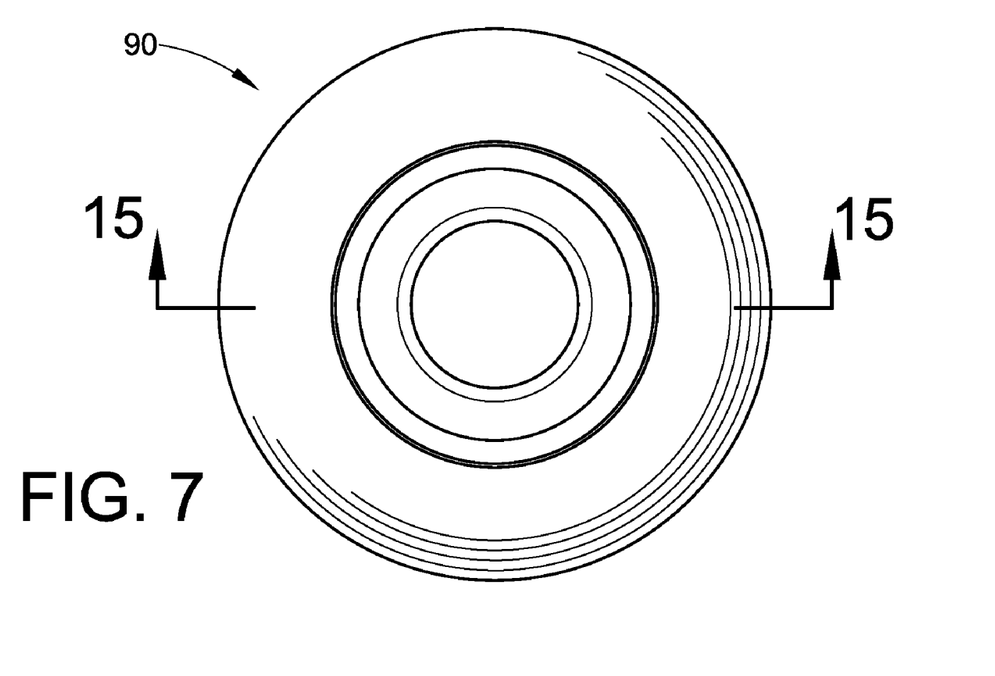
FIG. 7 is a top view of a nasal pillow.
Figure 8:
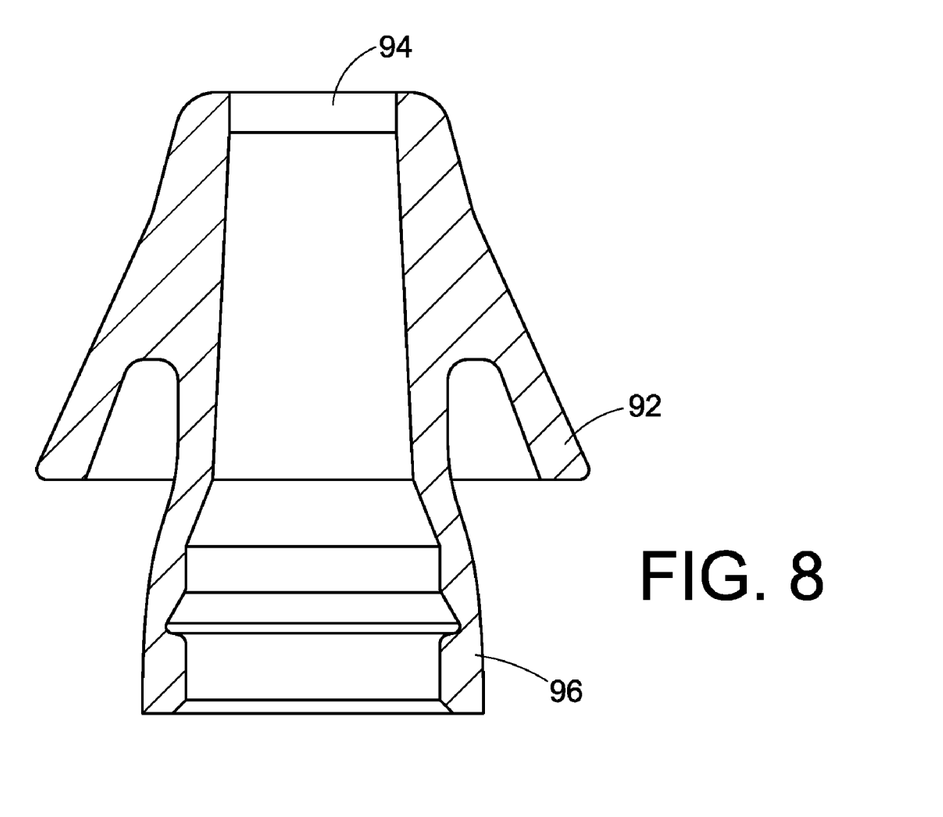
FIG. 8 is a cross-sectional view taken along lines 15-15 of FIG. 7.
Figure 9:
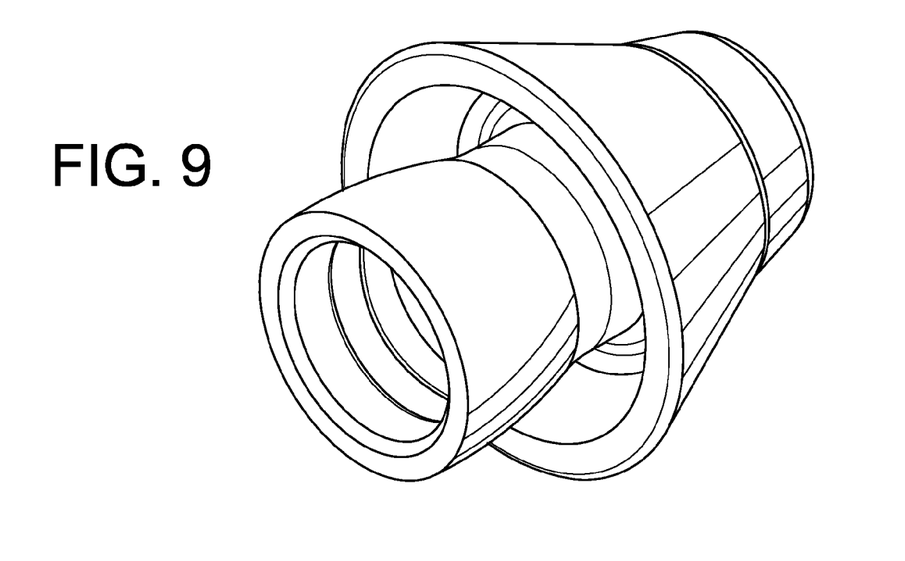
FIGS. 9 and 10 are perspective views of the nasal pillow.
Figure 10:
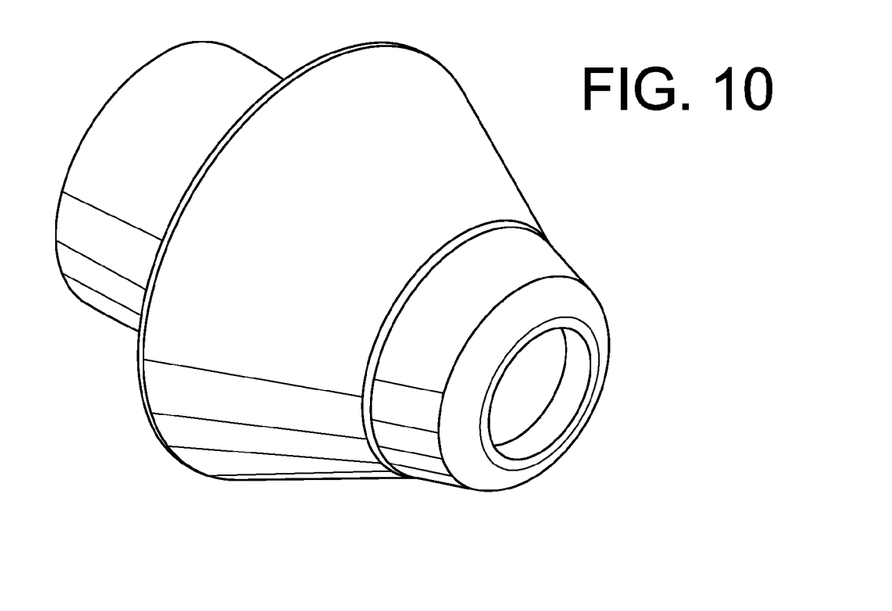

With attention to FIGS. 1 and 6, it can be seen that controller 16 comprises a pistol grip type handle having a flat base portion 80 sized to facilitate the system being independently supported in a standing position on a flat surface, and a hand portion 82. The upper portion 84 of the controller 16 comprises a housing for the fluid passageways and for attached support of the bottles 12, 14. Flexible nasal pillows 90 are received on the nasal pillow seats 48, 58.

Figure 5:
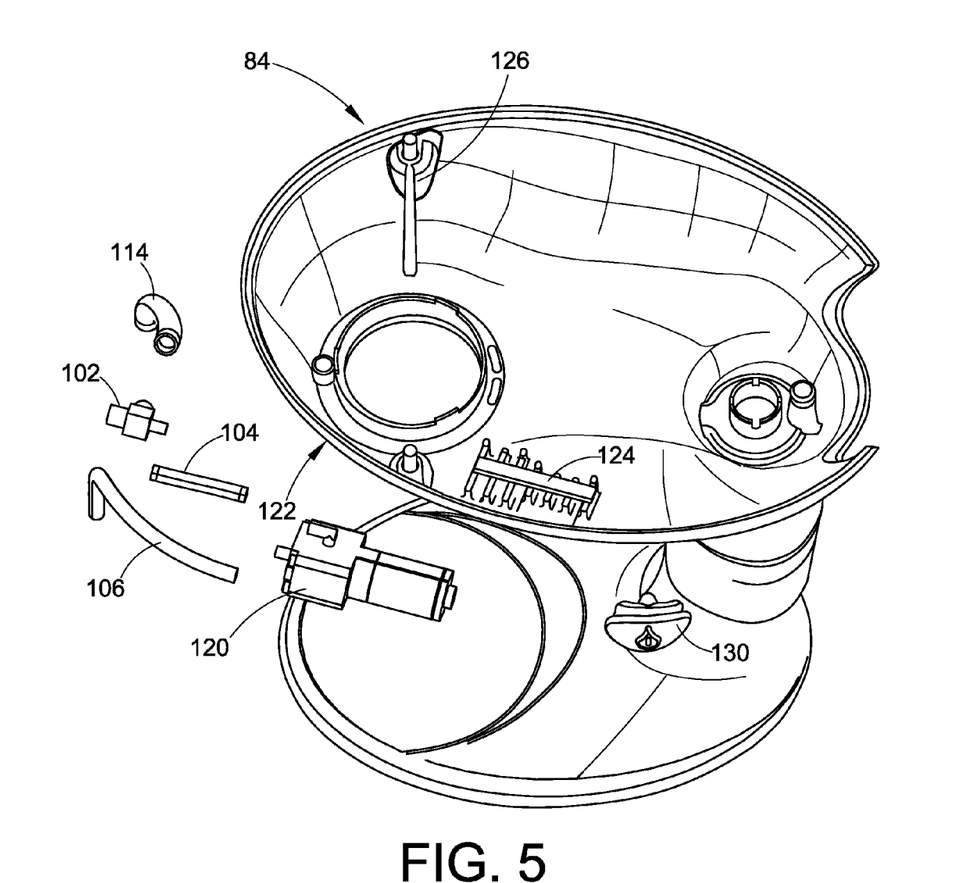
FIG. 5 is a partial exploded view showing the handle housing and pump.

Energy is supplied to the system via a disposable or rechargeable battery 92 in electrical connection with pump 120, although it is within the scope of the present embodiments that a corded transformer could similarly supply the energy to the pump. The system is turned on and off by operator control of a switch 94 on handle 82. Replacement of the batteries is facilitated by a door 98.

Vacuum is imparted to effluent bottle 14 by pump 120 drawing air from port 34 through evacuation tube 100, T-fitting 102, and pump supply inlet tube 104. Air is exhausted to atmosphere through exhaust tube 106. As a safety precaution to preclude excessive vacuum pressure in the effluent bottle 14 and its communication to the nasal cavity of a user, cracking valve 112 will open the effluent bottle to atmosphere through cracking valve tube 114 when the vacuum pressure in the system is between about −10 and −20 inches of water, and preferably −15 inches. A plurality of vents 122 are spaced about the perimeter of the upper housing 84 so that the cracking valve 112 can be exposed to atmosphere despite being contained within the controller 16. Pump 120 is supported within the housing by support ribs 124, and the cracking valve is supported by support rib 126. The cracking valve 112 is preferably a miniature umbrella valve intended to allow a vacuum limit that opens suddenly (cracks) at the preferred pressure limit without preliminary or graduated leaking.

An elastomeric cover 130 seals the pump control switch in the handle to resist the switch, batteries, and associated wiring within the housing.

There is a feature of the subject embodiment such that the fluid passageways in removable cartridge 40 can be reversed in order to reverse the flow through the nasal cavity. In other words, the presently illustrated embodiment shows that flexible tube 46 communicates the saline to first nasal pillow 130 (FIG. 6), while second nasal pillow 132 receives the effluent saline and communicates it to effluent bottle 14 through flexible tube 56. The flow direction through the nasal cavity can be reversed if flexible tube 46 is attached to second pillow 132 and flexible tube 56 is attached to first nasal pillow 130. According to the desires of a user, the user can select a cartridge, imparting the desired flow at each particular time of usage. In another embodiment, the nasal pillows 130, 132 would be situated on a turntable interface allowing for a reversal of the flow.

With reference to FIGS. 7-10, not only to preclude leakage, but also to facilitate flow with gentle pressures for enhanced therapeutic experience, nasal pillows or domes 90 must be dimensioned and flexible enough to sufficiently seal against a wide variety of anatomical variances per user. Accordingly, it is envisioned that the replaceable pillows are selectively removable from the cartridge 40 and would come in a variety of sizes, for example, small, medium, and large. In order to conform to varied nostril shapes, the domes include a flexible skirt 92, that is spaced from the central core and tapers towards the opening 94 to facilitate a seal as the dome 90 is inserted into the nostril. A female sleeve 96 elastomerically conforms about seats 48, 58 to preclude leakage between the dome 90 and the cartridge 40.

The foregoing embodiments are intended to operate in the following manner: the user lifts the device 10 and positions it so that the nasal pillows 90 are gently inserted into his or her nostrils. The conforming flexibility of the pillows makes a seal easy to achieve without having to force or jam the pillows into the nostrils. After inserting the device in a proper position, it should be noted that the supply bottle saline is disposed to provide positive pressure in the amount of approximately 6 inches of a water via gravity into the inlet fluid passageway 46 and the nasal cavity. Such a limited and diminishing amount of pressure by itself is not typically sufficient to induce a continuous flow of the saline through the nasal cavity into the effluent bottle 14. Accordingly, the user presses the switch 94 to turn on the pump 120 to generate a gentle vacuum in the amount of approximately −15 inches of water in the effluent bottle to further induce the flow of saline into the nasal cavity. Initiation of the saline flow requires the user's soft palate to be closed thus forming a closed system of the nasal cavity. This is a natural occurrence that for most users results merely by breathing through one's mouth. However, some users find it helpful or necessary to say "ahhh" or "kahhh" in order to close the soft palate and initiate flow. Once the flow has commenced into the effluent bottle, it will normally proceed continuously until the supply bottle 12 is empty, an occurrence that can be detected by the user visually and by sensing the cessation of saline into the nasal cavity. The entire therapeutic irrigation process is usually completed in between 15 and 30 seconds. The saline effluent can then be drained from the effluent bottle and thrown away. The nasal pillows 90 can be removed and washed, as can the cartridge 40. The effluent tube 56 can also be washed by a washing rinse or with a cleansing brush (not shown). The emptied supply bottle 12 can then be removed and stored, or readily attached to the receiving cap 20.

Accordingly, in less than a minute, a user has washed and irrigated the nasal cavity in a safe, gentle and very convenient manner without any of the mess of neti pots or squeeze bottles, and with consistent and safe regulation and control over the pressures induced into the nasal cavity itself.

The invention claimed is:

1. A nasal lavage device comprising:
a hand-held controller;
a gravity-fed source of saline solution received on the controller;
an effluent receptacle received on the controller;
a nasal interface configured for engaging nostrils of an associated user of the device wherein the source is above the nasal interface and provides gravity-fed flow of the saline solution through the nasal interface, and the receptacle is positioned below the interface;
a fluid passageway disposed to communicate the source of saline solution with the effluent receptacle from the nasal interface through a nasal cavity of the associated user; and
a cartridge selectively separable from the controller, wherein the cartridge comprises the nasal interface and at least a portion of the fluid passageway, wherein the nasal interface, the fluid passageway and the cartridge are all included in the controller and wherein removal of the cartridge from the controller disconnects the nasal interface from the source.

2. The nasal lavage device of claim 1 wherein the fluid passageway communicates the saline relative to the nostrils in a preselected direction.

3. The nasal lavage device of claim 2, wherein a second cartridge is disposed in place of the cartridge in the controller and includes a second fluid passageway disposed to communicate the saline solution in an opposite direction to the preselected direction relative to the nostrils of the user.

4. The nasal lavage device of claim 1 wherein the nasal interface comprises nasal pillows situated on a turntable interface allowing for a selective reversal of flow relative to the nostrils of the user.

5. The nasal lavage device of claim 1 wherein the nasal interface includes an elastomeric nasal pillow for flexible, sealing engagement against the user's nostril.

6. The nasal lavage device of claim 5 wherein the nasal pillow has a central core for facilitating selective receipt and removal from pillow seats disposed on the nasal interface.

7. The nasal lavage device of claim 1 wherein the source of saline comprises a separable bottle.

8. The nasal lavage device of claim 1 wherein the effluent receptacle comprises a separable bottle.

9. The nasal lavage device of claim 1 wherein the controller comprises a housing including a vacuum pump.

10. The nasal lavage device of claim 1 wherein the controller includes a pistol grip type handle.

11. A nasal lavage device comprising:
a hand-held controller having a pump;
a gravity-fed source of saline solution received on the controller;
an effluent receptacle received on the controller;
a nasal interface configured for engaging nostrils of an associated user of the device wherein the source is above the nasal interface and provides gravity-fed flow of the saline solution through the nasal interface, and the receptacle is positioned below the interface;
a fluid passageway disposed to communicate the source of saline solution with the effluent receptacle through a nasal cavity of the associated user; and
a cartridge selectively separable from the controller wherein the cartridge comprises the nasal interface and at least a portion of the fluid passageway, wherein the nasal interface, the fluid passageway and the cartridge are all included in the controller for communicating the saline with the nostrils and wherein removal of the cartridge from the controller disconnects the nasal interface from the source.

12. The nasal lavage device of claim 11 wherein the controller includes a pistol grip type handle.

13. The nasal lavage device of claim 11 wherein the pump urges the saline solution through the fluid passageway and the nasal cavity.

14. The nasal lavage device of claim 11 wherein the nasal interface comprises nasal pillows situated on a turntable interface allowing for a selective reversal of flow relative to the nostrils of the user.

* * * * *